(12) United States Patent
Lever et al.

(10) Patent No.: US 10,542,911 B2
(45) Date of Patent: Jan. 28, 2020

(54) SYSTEM AND METHOD FOR LARYNGEAL REFLEX EXAMINATION

(71) Applicants: Teresa Lever, Columbia, MO (US); Cameron Hinkel, Columbia, MO (US)

(72) Inventors: Teresa Lever, Columbia, MO (US); Cameron Hinkel, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 1134 days.

(21) Appl. No.: 14/862,573

(22) Filed: Sep. 23, 2015

(65) Prior Publication Data

US 2016/0081591 A1     Mar. 24, 2016

Related U.S. Application Data

(60) Provisional application No. 62/071,438, filed on Sep. 23, 2014, provisional application No. 62/142,230, filed on Apr. 2, 2015.

(51) Int. Cl.
   *A61B 5/08*      (2006.01)
   *A61B 5/11*      (2006.01)
   *A61B 5/00*      (2006.01)

(52) U.S. Cl.
   CPC .......... *A61B 5/1104* (2013.01); *A61B 5/0053* (2013.01); *A61B 5/08* (2013.01); *A61B 5/6852* (2013.01); *A61B 5/1121* (2013.01)

(58) Field of Classification Search
   CPC ........ A61B 5/08; A61B 5/1104; A61B 5/0053
   See application file for complete search history.

(56) References Cited

PUBLICATIONS

Domer, et al. Neurophysiology and Clinical Implications of the Laryngeal Adductor Reflex. Curr Otorhinolarygol Rep. ; 1(3): 178-182 . Sep. 2014. (Year: 2014).*
Ulualp. Mapping Regional Laryngopharyngeal Mechanoreceptor Response. Clinical and Experimental Otorhinolaryngology. vol. 7, No. 4: 319-324, Dec. 2014. (Year: 2014).*
Martin et al, "Laryngopharyngeal Sensory Discrimination Testing and the Laryngeal Adductor Reflex", 1999, Ann Otal Rhinol Laryngol 108, p. 725-730 (Year: 1999).*

* cited by examiner

*Primary Examiner* — Christian Jang
(74) *Attorney, Agent, or Firm* — Sandberg Phoenix & von Gontard PC

(57) ABSTRACT

A system for elucidating physiological characteristics of laryngeal adductor reflex (LAR) responses in a human or animal subject's larynx's vocal folds (VFs) includes a pressure pulsing component to provide a stable and adjustable pulse of pressure to the larynx, a control system component in functional communication with the pressure pulsing component to control or regulate one or more aspects of the timing, magnitude and number of pulses of pressure delivered by the pressure pulsing component during respiratory cycles, and a respiratory sensor component to detect and/or determine physiological characteristics of the subject's LAR response. The method includes evoking a LAR response in the subject and determining one or more physiological measurements including duration, velocity, and angles of motion of the subject's VFs during the LAR response. The present disclosure provides for enhanced endoscopic field of view of the larynx and delivering stimuli over a wider range of controlled parameters.

18 Claims, 9 Drawing Sheets

SYSTEM AND METHOD FOR LARYNGEAL REFLEX EXAMINATION

CROSS-REFERENCE TO RELATED APPLICATIONS

This application claims priority to U.S. Patent Application No. 62/071,438, titled "Air Pulse Device for Laryngeal Reflex Examination", filed Sep. 23, 2014, and 62/142,230, titled "Air Pulse Device and Protocol for Laryngeal Reflex Examination", filed Apr. 2, 2015, the disclosures of which are incorporated herein by reference in their entirety, including any attachments thereto.

STATEMENT REGARDING FEDERALLY SPONSORED RESEARCH OR DEVELOPMENT

Not applicable.

FIELD

The present disclosure relates to systems, methods and devices for conducting Laryngeal Reflex Examinations, and more specifically to systems and methods suitable to perform in-depth evaluation/examination of the laryngeal adductor reflex (LAR) to determine physiological characteristics of a subject (animal or human) such as by use of air pressure pulse delivery.

BACKGROUND

The statements in this section are intended to provide background information related to the present disclosure and do not constitute prior art.

The laryngeal adductor reflex (LAR) entails brief bilateral closure of the true vocal folds (VFs) in response to mechanical or chemical stimulation of the laryngeal mucosa. This defensive airway reflex provides protection from material inappropriately entering the lungs. It is therefore no surprise that LAR impairment correlates with pharyngeal dysphagia and aspiration, as well as other conditions, which are highly correlated with morbidity and mortality.

The clinical procedure for evaluating the LAR is air-pulse laryngopharyngeal sensory testing, performed as part of a flexible endoscopic evaluation of swallowing. This procedure entails transnasal passage of a flexible laryngoscope, typically without topical anesthesia, to deliver air pulses to the arytenoid mucosa and/or other mucosal targets at the entrance of the larynx (e.g., aryepiglottic folds), with left/right sides tested separately. An air-pulse device, such as the AP-4000; Vision Sciences, Pentax, and Medtronic, is used in this procedure to generate pulses of air between 50-millisecond to 1-second durations at incrementally increasing pressures, ranging from approximately 2 to 10 mm Hg. Air pulses are delivered through the endoscope working channel or side channel sheath, with the endoscope tip positioned 1 to 2 mm away from the arytenoid mucosa and other mucosal targets at the laryngeal entrance. This extremely short working distance limits visualization to only the ipsilateral arytenoid or other mucosal targets, which restricts quantification to a single metric: threshold air pressure that evokes ipsilateral medialization of the arytenoid or other mucosal targets, determined separately for each side. Requiring pressures >4 mm Hg to evoke a response or having an asymmetric or absent response is suggestive of sensory pathology, although it is not pathognomonic for any specific disease process.

LAR impairment has been identified in numerous conditions and pathologies, such as Parkinson's disease, cerebrovascular accident, chronic cough, adductor spasmodic dysphonia, and acid reflux disease, among others. In amyotrophic lateral sclerosis (ALS), 54% of cases have elevated sensory thresholds (>4 mm Hg), which suggests that LAR impairment can be a major contributing factor of aspiration pneumonia, a leading cause of death in this disease. LAR impairment has also been identified in healthy aging individuals, with progressive increases in pressure thresholds occurring each decade of life. This finding corresponds with increased incidence of silent aspiration in healthy older individuals, placing them at risk for aspiration pneumonia. Despite the negative outcomes associated with LAR impairment, effective treatments are lacking, likely due at least in part to limitations in the clinical procedures to evaluate the LAR and the limited scientific knowledge of underlying pathological mechanisms.

Some research has been done to improve the commercial AP-4000 system. However, these attempts/devices are regulated air pressure systems that manually trigger air pulses by opening a solenoid valve to release pressurized air from a reservoir. This pressurized air is delivered through a channeled endoscope into the throat of a patient to target the mucosa at the entrance of the larynx, which is innervated by the superior laryngeal nerve. Mechanical stimulation of this area evokes the laryngeal adductor reflex (LAR), identified as brief closure of the vocal folds to protect the airway. All of these devices permit measurement of a single metric: threshold pressure that evokes the LAR. Ranges for normal and abnormal pressure threshold responses have been defined using predicate air pulse devices. Abnormal threshold responses are indicative of laryngeal pathology but not pathognomonic for any specific disease process.

SUMMARY

The present disclosure provides new and improved LAR testing systems and methods for determining an array of useful physiological characteristics of a subject's vocal folds and their LAR response, with enhanced endoscopic field of view of the larynx and by delivering stimuli over a wider range of pressures. Thus, the inventive LAR system can provide additional metrics to improve the usefulness of LAR testing in clinical practice and research.

In various embodiments of the present disclosure, a method is provided for performing an LAR test on a subject, wherein the subject has a larynx, including left and right vocal folds which undergo adduction, or closure along the medial edge of both vocal folds (or incomplete medialization along the edge), and abduction, or re-opening of the vocal folds. The method includes the steps of evoking a LAR response and determining one or more physiological measurements of duration, velocity, and angles of motion of the subject's VFs during the LAR response.

In various other embodiments of the present disclosure, a LAR testing system is provided which includes an enhanced and adjustable pressure pulse delivery system to evoke and visualize the bilateral LAR responses in a subject having a larynx (such as a mammal, including a mouse or human). The inventive (generally, air) pulse system is designed to deliver stimuli over a wide range of pressures, and can deliver a stimulus via manual or automated operation, including a train stimulus option. Thus, in various embodiments, the pressure pulse system of the present disclosure can provide a repeatable stimulus for LAR testing and involves the measurement of a variety of physiological characteristics, including the duration, velocity and angles of VF motion during the LAR. Furthermore, the inventive air pulse system can account for temporal variation in the LAR response and the stimulus relative to the respiratory cycle and perform automatic delivery of stimuli in synchrony with the respiratory cycle of a subject.

In yet other embodiments, the inventive system includes an air or other stimuli pressure system configured to provide a stable and adjustable source of pressure pulses, a control system component in electronic or other functional communication with the pressure system and a respiratory sensor component to control and regulate the timing and quantity of the stimuli delivery. The inventive pressure pulse system can further include an air catheter unit in communication with the pressure system to deliver air pulses to the laryngeal mucosa of a subject, which in various embodiments provides enhanced air quality, including air from which debris and other particles has been reduced or essentially removed.

The inventive system and method also includes test procedures for determining a variety of novel LAR metrics beyond and/or in addition to the threshold air pressure measurement determined by existing devices, which further monitors and quantifies the bilateral LAR responses in a subject. These novel LAR metrics include, but are not limited to, VF adduction phase duration, glottic closure duration, VF abduction duration, total LAR duration, and LAR onset latency. These parameters further facilitate differential diagnosis of laryngeal pathology.

BRIEF DESCRIPTION OF THE FIGURES

The presently disclosed subject matter will be better understood from reading the following description of non-limiting embodiments, with reference to the attached drawings and figures described and included herewith, which are for illustration purposes only and are not intended to limit the scope of the present teachings.

FIG. 6A (left) shows an image obtained using a prior art LAR protocol with 1 to 2 mm of working distance and a small field of view. FIG. 6B (right) is an image obtained using the LAR protocol of present the invention, e.g., with a larger working distance and field of view, in accordance with various embodiments of the present disclosure.

Corresponding reference numerals indicate corresponding parts throughout the several views of the drawings.

DETAILED DESCRIPTION

Figure 1:
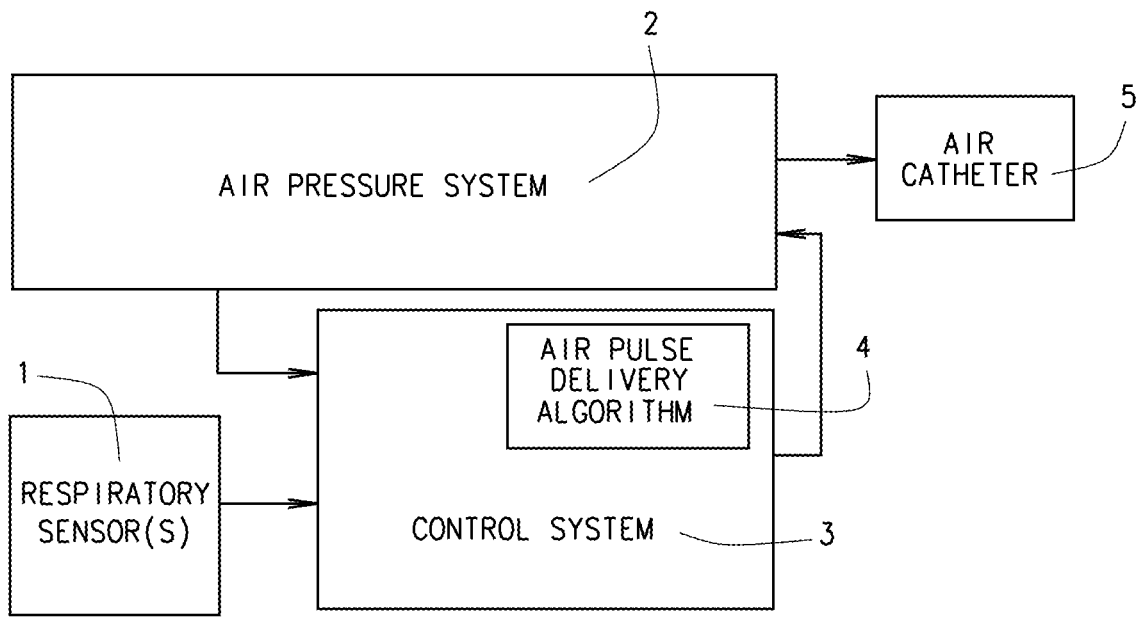
FIG. 1 is a block diagram of an air pulse system, in accordance with various embodiments of the present disclosure.

The foregoing summary, as well as the following detailed description of various embodiments will be better understood when read in conjunction with the appended drawings and figures. As used herein, an element or step recited in the singular and proceeded with the word "a" or "an" should be understood as not excluding the plural of said elements or steps, unless such exclusion is explicitly stated. Furthermore, references to "various embodiments" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property can include additional such elements not having that property.

The following description is exemplary in nature and not intended to limit the present teachings, applications, or uses, especially to other embodiments employing the teachings and discoveries disclosed herein. Throughout this specification, like reference numerals will generally be intended to be used to refer to like elements.

The present disclosure provides an air or other pressure pulse system to deliver manually triggered or automated air pulses to the larynx of subjects having a larynx with vocal folds, including rodents, humans, and other mammals to elicit the laryngeal adductor reflex (LAR), e.g., in awake or lightly sedated subjects. The inventive pulsing system is capable of delivering repeatable stimuli over a wide range of pressures and if desired, in synchrony with the respiratory cycle of a subject. In various embodiments, the inventive system includes at least three subsystems or components: i) a pressure pulsing system or component configured to provide a stable and adjustable air pressure source, ii) a respiratory sensor unit or component, and iii) a control system unit or component in electronic or other functional communication with the pressure system and in various embodiments the respiratory sensor unit component, which is configured to control and regulate the timing and quantity of the stimuli delivered, e.g., through use of an algorithm employed for that purpose. The inventive pressure pulsing system can further comprise an air catheter connecting with the air or other stimuli pressure pulsing system to deliver an air pulse of enhanced quality to the laryngeal mucosa of a subject.

Referring to FIG. 1, which is a block diagram of various embodiments of the inventive system, in such embodiments the system comprises one or more respiratory sensor unit 1, an air pressure system 2, and a control system 3 that is structured and operable to control and regulate the force, timing and other aspects of the delivered pulse, such as an air pulse delivery algorithm 4. The control system 3 can be in electronic communication with the respiratory sensor unit 1 and the air pressure system 2. In various embodiments, an air catheter unit 5 can be connected to the air pressure system 2 to enhance the purity of the air delivered, and in various embodiments, provide essentially, if not completely, debris-free air pulses.

Several different types of peripheral sensors can be employed as the respiratory sensor unit 1 to interface with the control system 3 to measure the respiratory cycle. Exemplary sensors can include i) mechanical transducers (e.g., piezo respiratory belts) that deflect with movements of the chest wall, ii) infrared distance sensors that measure the distance between the sensor and the chest wall, and iii) laser distance sensors that measure the distance between the sensor and the chest wall. The design of other types of sensors are known to or within the purview of those skilled in this art.

Figure 2:
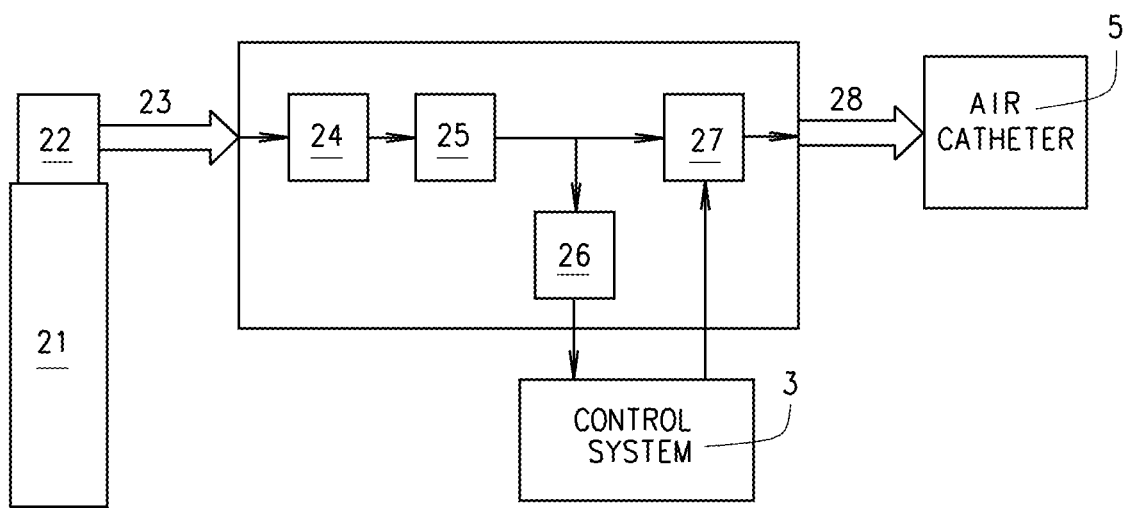
FIG. 2 is a schematic diagram illustrating the air pressure system portion of the air pulse system of FIG. 1, in accordance with various embodiments of the present disclosure.

FIG. 2 is a schematic diagram of the air pressure system shown in the air pulse system of FIG. 1, in accordance with various embodiments of the present disclosure. As illustrated, in such embodiments, the air pressure system 2 is an air circuit modified upon the existing designs to provide a stable source of air pressure that is readily adjusted by an operator (manual or automated). As shown in FIG. 2, the air pressure system 2 can further comprise at least the following components: i) a high pressure source 21, ii) a primary regulator 22, iii) input air tubing 23, iv) a secondary regulator(s) 24, v) air reservoir(s) 25, vi) pressure transducer(s) 26, vii) solenoid valve(s) 27, and viii) output air tubing, 28. Also shown, as depicted in the embodiment illustrated in FIG. 2, the pressure transducer 26 and the solenoid valve 27 are interfaced with the control system 3.

More specifically, the high pressure source 21 can be, e.g., a medical air cylinder. Alternatively, in other embodiments, the high pressure source 21 can be an air cartridge, or a mini air cartridge. The primary regulator 22 can be employed to reduce the air pressure of 21 to a level suitable for downstream system components. The input air tubing 23 can connect 22 to the secondary regulator 24, whereas 24 can be user controlled and sets the pressure at the reservoir 25. The pressure transducer 26 can be used to measure pressure at 25. The solenoid valve 27 is an electromechanical valve, controlled by the control system 3, and can be used to release air from 25 to the output air tubing 28. The output air tubing 28 can be used to connect the air output on the device enclosure directly to the working channel of an endoscope or, in various embodiments, to an air catheter unit 5 which is passed through the working channel of an endoscope.

Figure 3:
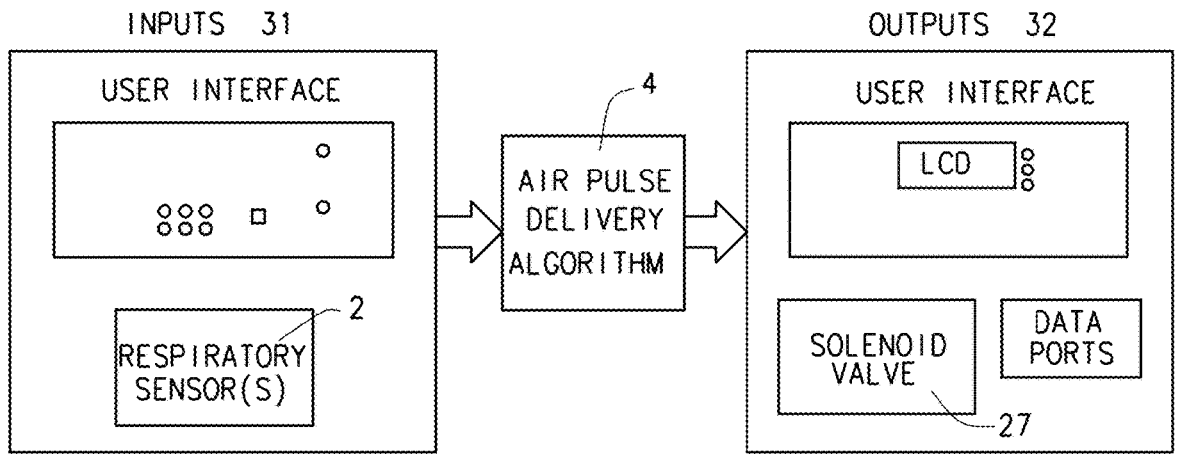
FIG. 3 is a schematic diagram of the control system of the air pulse system of FIG. 1, in accordance with various embodiments of the present disclosure.

Referring to FIG. 3, which is a schematic diagram of the control system 3 of the air pulse system of FIG. 1, the control system 3 facilitates the user interface and performs control and regulatory functions, e.g., via the control algorithms (such as the pulse delivery algorithm 4 described below) executable by at least one processor of the control system 3. As shown in FIG. 3, a user interface of the control system 3, can include an input unit 31 for the operator/user to adjust settings (manually or automatically) and an output unit 32 to provide feedback regarding the operator settings and sensor readings. The control algorithms/air pulse delivery algorithm 4 are based on operator settings and sensor readings.

More specifically, the input unit 31 can be configured to collect two sets of inputs, from the respiratory sensor unit 1 and from the user interface. The signal from the respiratory sensor unit 1 is, e.g., bandpass filtered and amplified before reaching the controller. The user interface can include, e.g.: i) a manual air pulse button sending a single on/off signal to the solenoid valve 26 when pressed, ii) an automatic air pulse switch—when switched on, the controller outputs a periodic train of on/off signals to the solenoid valve 26, iii) a gain knob which increases or decreases amplification of the respiratory signal, iv) an array of air pulse duration controls that increase or decrease the duration of the air pulse signal, e.g., ranging from about 25 milliseconds to about 2 seconds, whereas the setting applies to either/both manual air pulses and automatic air pulses, v) an array of air pulse interval controls that increases or decreases the nominal period of time between subsequent automatic air pulses, ranging, e.g., from about 2 to about 30 seconds, and vi) an array of air pulse phase controls that define at what phase of the respiratory cycle automatic air pulses will be delivered.

Figure 4:
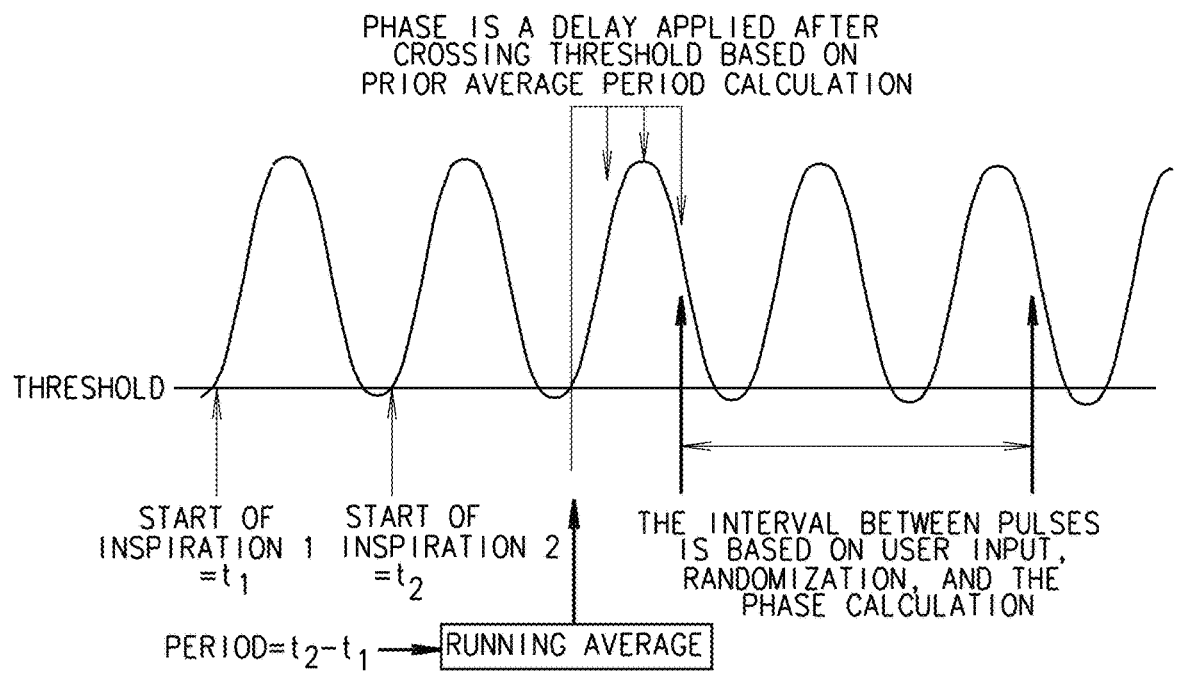
FIG. 4 is an illustration of an exemplary waveform generated by execution of an air pulse delivery algorithm by the system illustrated in FIG. 1, in accordance with various embodiments of the present disclosure.
Figure 5:
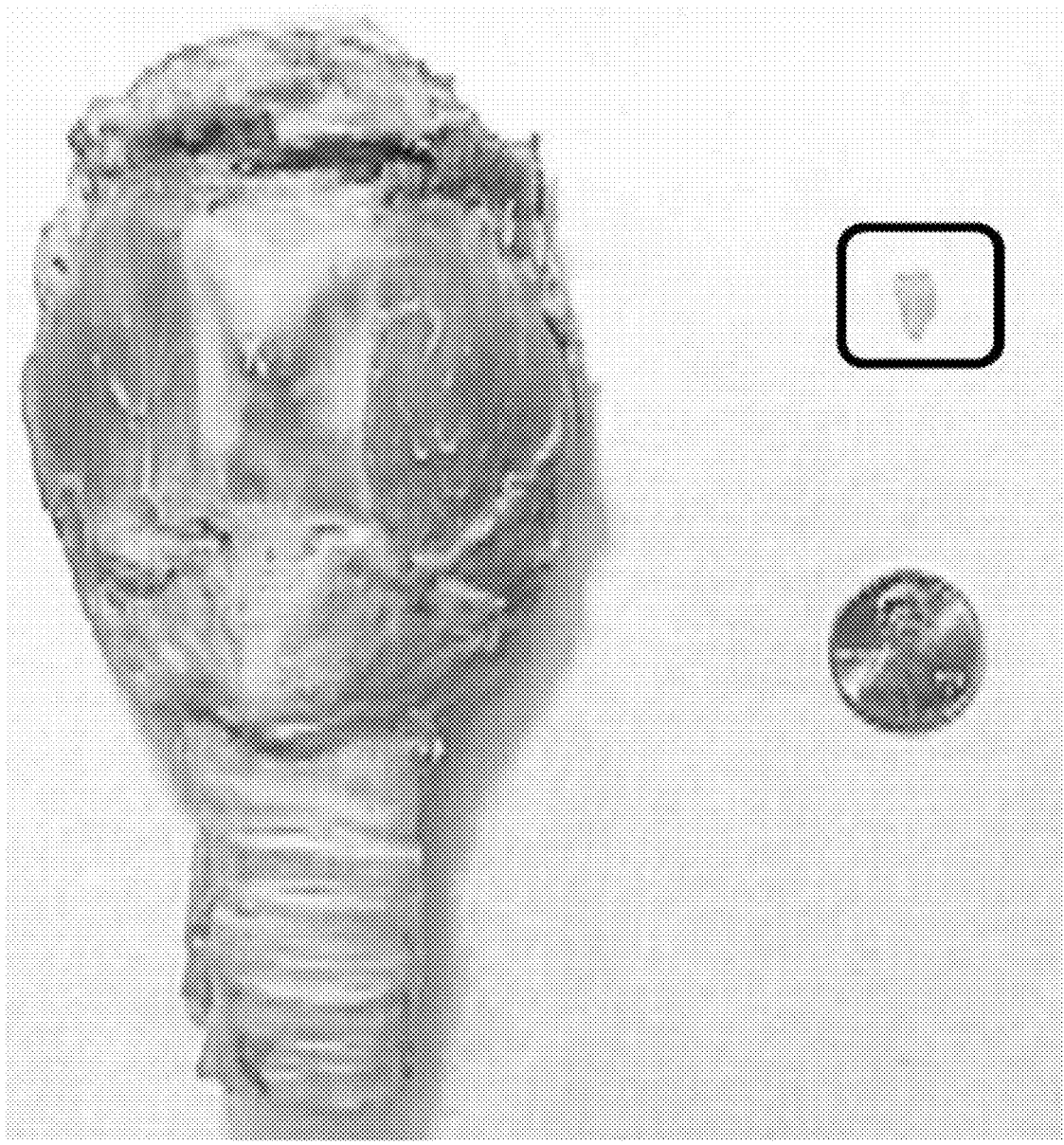
FIG. 5 depicts images of human and mouse larynxes in comparison to a penny. This Figure highlights the enormous size difference between the mouse larynx (black box) and human larynx (left), with a Lincoln penny shown for comparison. The inventive air pulse system shown in FIG. 1 is suitable for LAR testing in a wide range of species with various sized larynges, in accordance with various embodiments of the present disclosure.

The air pulse delivery algorithm 4, as executed by the one or more processors, can use as inputs a combination of user defined settings and/or calculations based on sensor data to determine, e.g., output, the specific parameters for opening and closing the solenoid valve 27 to release air pulses. FIG. 4 provides an exemplary illustration of a pulse signal, or respiratory rate waveform, output by the air pulse delivery algorithm.

Respiratory rate calculations, e.g., the respiratory waveform, output by the control system 3, via execution of the air pulse delivery algorithm 4, can utilize one or more of the following non-limiting factors:
  i) The respiratory signal is pre-processed with filtration and amplification to enhance the signal,
  ii) The start of the subject's inspiration is determined by detecting a threshold voltage crossing of the respiratory signal. This small threshold level is higher than zero volts, i.e., it should be above the noise level of the circuit,
  iii) Each threshold crossing on an upslope is time-stamped as the start of an inspiration,
  iv) The difference between each new threshold crossing and the previous threshold crossing can be used to calculate the period of that respiratory cycle,
  v) A moving average can be applied to smooth the period calculation, and
  vi) The respiratory rate can then be calculated from the average period.

The respiratory rate calculation, e.g., the respiratory waveform output by the control system 3 can be used to determine when in the respiratory cycle to deliver the air pulse signal. The respiratory waveform is analyzed for parameters such as peak and trough levels and velocities. The signal peak represents end of inspiration; the signal trough represents end of expiration. Using such parameters in combination with the respiratory rate, any point in the respiratory cycle can be predicted based on the threshold crossing of the next cycle. Because the period is calculated using a moving average, it provides a dynamic, but relatively stable estimate of the current respiratory rate.

In various embodiments, the respiratory phase calculation, can further utilize the operator-defined phase and a delay applied upon threshold crossing before signaling the solenoid to open.

Using a randomized interval factor inserted between air pulses can apply a degree of randomization to the nominal interval between air pulses. Thus, a randomized interval is the nominal interval plus or minus some small, or incremental, period of time used to create the randomizing effect. A new randomized interval can thus be determined after each air pulse signal is delivered.

In various embodiments, the respiratory phase calculation is used in combination with the randomized interval between air pulses to calculate the exact timing of an automatic air pulse signal delivery. In various embodiments, the randomized interval is the minimum possible time between subsequent air pulses. Once this interval has been met, the controller/user waits for the next threshold crossing and then applies the delay determined by the respiratory phase calculation.

In various embodiments, the aforesaid output unit 32 interfaces/communicates with the solenoid valve 26 by sending electromechanical on/off signals to the solenoid valve 26. Square pulses of variable duration can be set by the operator/user, whereas triggering can be manual or determined by execution of the air pulse delivery algorithm.

In various implementations, the output unit 32 further comprises a user interface including an LCD screen to display various data such as pressure reading from 25, respiratory rate calculated, air pulse duration, interval, and phase. The interface can also include an array of indicator lights to signal i) air pulse delivery (e.g., lights up every time an air pulse is delivered (manual or automatic), ii) clipping, e.g., can indicate the gain on the respiratory sensor is too high and should be manually reduced, such as when the respiratory signal rises above 4.8 volts, and/or iii) respiratory signal, e.g., an indicator lights up at the start of a subject's inspiration and turns dark at the end of subject's expiration. Optionally, the interface can further include other output ports to interface with peripheral computer based devices structured and operable to execute data acquisition software.

The air catheter unit 5 can also be used in the protocols for LAR testing. For example, it can include semi-rigid tubing inserted through the working channel of an endoscope to provide a sterile conduit to deliver reduced or essentially, or completely, debris-free air pulses to the laryngeal mucosa. In various embodiments, the tubing length can be sufficiently long to extend several mm beyond the distal opening of the working channel. The tubing can also be designed with incremental distance markers at discrete measurement intervals (e.g., cms) spaced along the entire length of the catheter tubing. In various embodiments, the outer diameter is maximized to the endoscope working channel, while the inner diameter is maximized while still providing adequate rigidity for manipulation by the endoscope to direct air pulses.

In various embodiments, the air catheter unit 5 can further comprise a blunt tipped Luer-lock needle. The blunt end of the needle is insertable into one end of the catheter tubing. The free end of the catheter tubing is then inserted into the endoscope's working channel. In such embodiments, the Luer-lock end of the needle is connected to the output air tubing 28.

The present disclosure further provides a method of determining useful physiological characteristics of the vocal folds and the LAR by measuring durational aspects, velocities and VF angles of the LAR, never before measured as components of the LAR. These physiological measurements can be obtained, e.g., by test procedures or protocols using the air pulse system described herein. More particularly, the air pulse system, as described herein, is structured and operable to monitor and quantify a variety of physiological characteristics of and determinations for the bilateral LAR responses in a subject having a larynx. As described herein, during implementation of the various protocols utilizing the air pulse system described above, various adjustments can be made to enhance the methods for measuring various aspects of physiological characteristics of LAR activity, e.g., VF durational, velocity and angle, etc. Such adjustments can include: (1) adjusting the working distance by positioning the endoscope tip more rostrally (or otherwise) to assist in visualizing the bilateral VFs during the entire procedure or, e.g., obtaining this effect by use of compensating scopic tools; and/or (2) adjusting the delivery of air pulses by the air pulse system to the arytenoid mucosa (or other mucosal targets, e.g., aryepiglottic fold) through small-diameter PE tubing inserted through the endoscope working channel, which deliver reduced or debris-free air pulses to the laryngeal mucosa of a subject. These modifications and others, utilized in various embodiments, can assist in quantification of a variety of LAR physiological metrics well beyond the one metric (threshold air pressure level) that can be measured by known LAR systems. The LAR metrics envisioned and disclosed herein include, but are not necessarily limited to, determinations of duration, velocity and angles, such as VF adduction phase duration, glottic closure duration, VF abduction duration, total LAR duration.

The novel LAR metrics can further facilitate differential diagnosis of laryngeal pathology. These diagnostic and clinical applications include testing for functional biomarkers and/or indicia of at least the following known pathologies and conditions associated with abnormal LAR activity: abductor paresis and paralysis, acid reflux condition or disease, adductor spasmodic dysphonia, amyotrophic lateral sclerosis (ALS), aspiration, aspiration pneumonia, cerebrovascular accident, chronic cough, cough reflex impairment, dysfunctional aspiration of the elderly, dysphagia, laryngeal penetration, Parkinson's disease and sleep apnea. LAR impairment is a symptom and/or contributor that can serve as a functional biomarker for these various conditions with LAR abnormalities.

This written description uses examples to disclose the various embodiments of the present disclosure and also to enable any person skilled in the art to practice the various embodiments of the present disclosure, including making and using any devices or systems and performing any incorporated methods. The patentable scope of the various embodiments of the present disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

EXAMPLES

Without further elaboration, it is believed that one skilled in the art can, using the preceding description, utilize the present invention to its fullest extent. The following specific examples are offered by way of illustration and not by way of limiting the remaining disclosure.

Methods

Example 1: Human LAR Test Procedure

Twenty healthy, non-smoking human subjects (7 males and 13 females) aged 20-40 were recruited and tested between May and October of 2014. Exclusionary criteria included the following self-reported medical conditions: laryngeal pathology, neurological conditions, heart disease, gastroesophageal reflux disease (GERD), recent or current upper respiratory symptoms, and current use of anticoagulant medications. Informed consent was obtained.

Figures 6A, 6B:
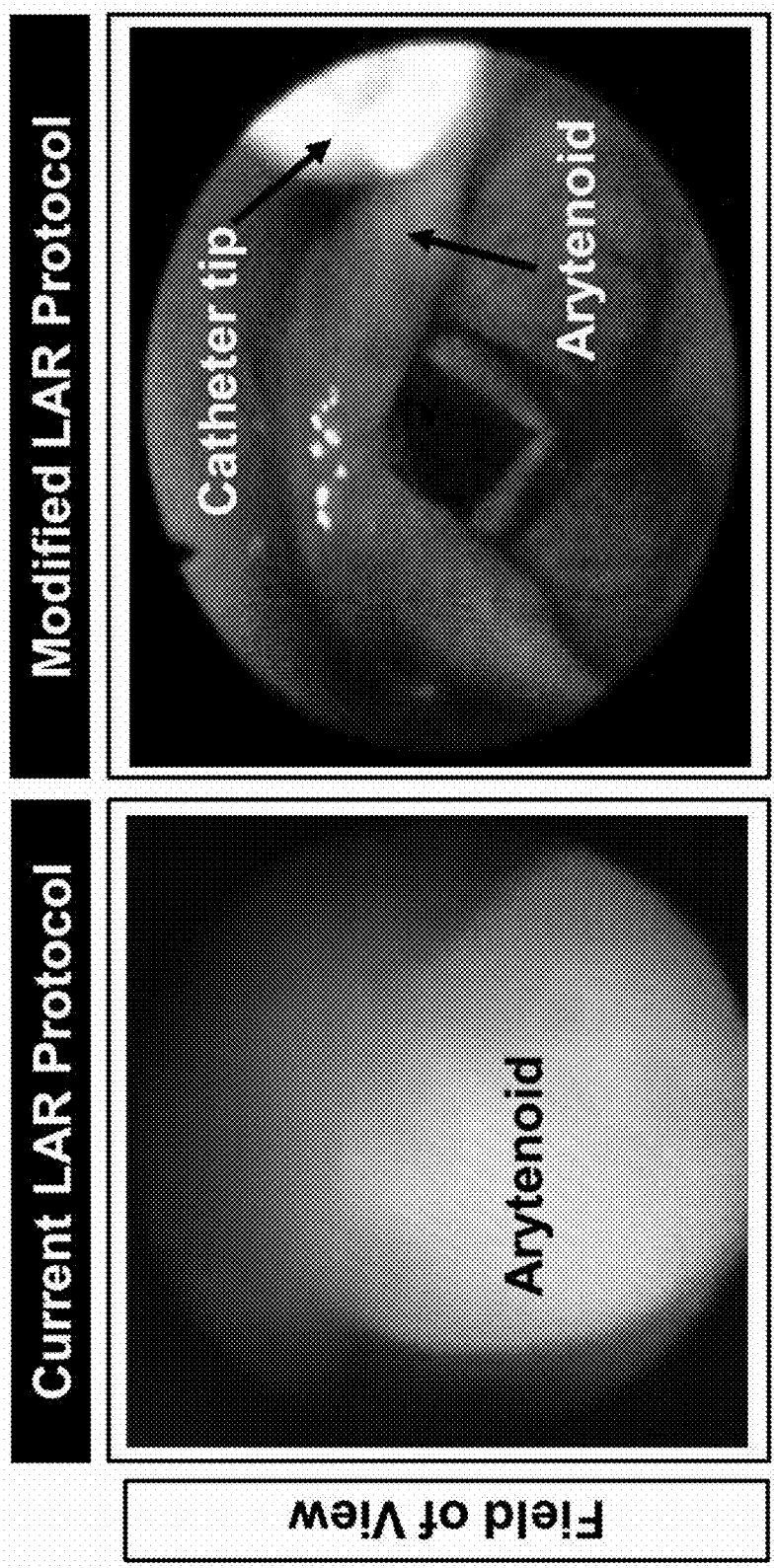
FIGS. 6A and 6B show images of the human laryngeal adductor reflex (LAR) testing.

The LAR test procedure entailed nasal administration of aerosolized oxymetazoline, followed by transnasal passage of a flexible 3.7 mm outer diameter (OD) endoscope with a 1.5 mm inner diameter (ID) working channel (11302BD2, Karl Storz). The endoscope interfaced with a Storz Tele Pack X system to provide real-time visualization and digital recordings. The endoscope tip was positioned at a typical level for viewing laryngeal pathology to permit visualization of the bilateral VFs throughout the procedure (FIG. 6(A) and (B)). Polyethylene (PE) tubing (1.22 mm OD, 0.76 mm ID, cut into uniform lengths of 100 cm) was inserted through the working channel of the endoscope and advanced until the distal tip was visible in the endoscopic field of view. The proximal end of the PE tubing was connected to the air-pulse delivery system via a 22-gauge blunt-tip Luer-lock needle. The purpose of the PE tubing was to amplify the pressure of each air pulse to enable supramaximal air pulse stimulation of the arytenoid mucosa (or other mucosal targets at the laryngeal entrance) from a greater working distance. The tubing could also be advanced closer to the arytenoid mucosa (and other mucosal targets) as needed, without altering the field of view. Air pulses were delivered to the left arytenoid mucosa at a rate of approximately one pulse every 10 seconds until 5-10 bilateral LAR responses were elicited. The entire procedure was digitally recorded at 30 frames per second (fps) and stored as MPEG-4 video files.

Bilateral LAR responses were evoked and recorded from 13 subjects (6 males and 7 females). As this was a research study on healthy volunteers and did not directly benefit the subjects, any discomfort resulted in termination of the procedure. This was the case for the remaining 7 subjects who experienced discomfort with passage of the endoscope.

Example 2: Mouse LAR Test Procedure

Three strains of mice from established colonies at the University of Missouri were included in this study: 1) transgenic SOD1-G93A mice on a C57/SJL background, 2) nontransgenic C57/SJL mice, and 3) wild-type C57BL/6 (or B6) mice. All mice were tested only once. Transgenic mice were tested after reaching disease onset, between 4 and 8 months of age. Nontransgenic littermates were age-matched with transgenic mice (i.e., between 4 and 8 months old). B6 mice were divided into two age groups: young (4-8 months) and old (12-18 months). Young B6 mice and nontransgenic SOD1-G93A mice served as a combined healthy control group for comparison with transgenic SOD1-G93A and aging B6 mice. Approximately 50 mice were utilized in this study, the majority for design and development of our air pulse system and LAR protocol rather than data collection.

Figure 7:
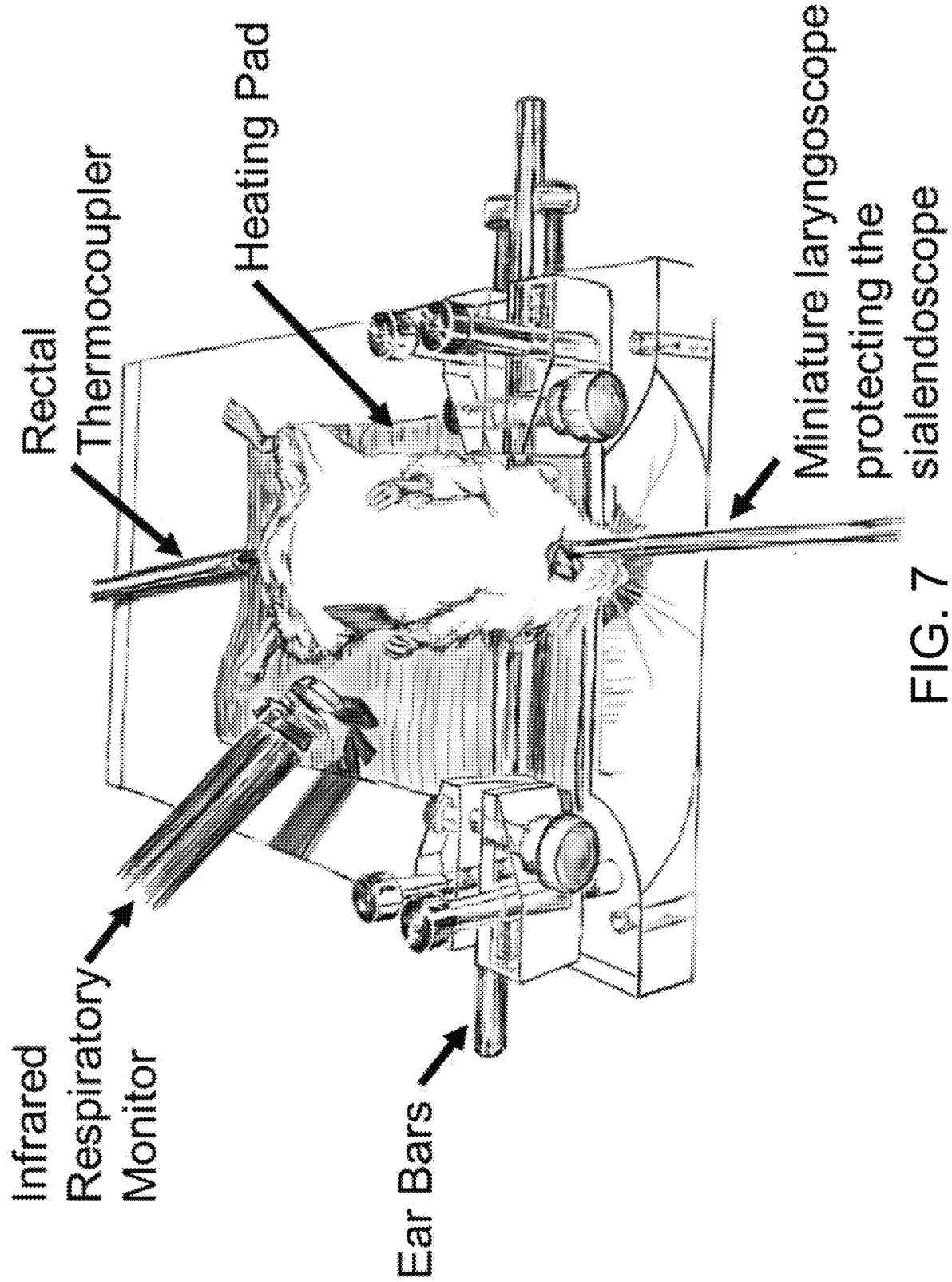
FIG. 7 is a schematic depiction of a murine laryngeal adductor reflex (LAR) setup, wherein an anesthetized mouse is shown undergoing LAR testing on a custom platform with labeled components, in accordance with various embodiments of the present disclosure.

Unlike humans, mice are unable to tolerate laryngoscopy without sedation. Therefore, we administered subcutaneous (SQ) injections of ketamine/xylazine/acepromazine dosed at 80/10/2 mg/kg. This anesthesia regimen resulted in a rapid induction time (<10 minutes) that persisted for ~1 hour on room air with extinguished deep pain reflexes (e.g., pedal withdrawal reflex). Anesthetized mice were tested in dorsal recumbency on a custom test platform after an overnight (6-12 hour) food restriction to prevent gastric reflux. Eyes were lubricated to prevent drying. The head was immobilized in ear bars secured to the test platform. Core body temperature was maintained at 37.0±0.2° C. using a rectal thermocoupler heating pad system. A schematic of the LAR test environment is shown in FIG. 7.

Figure 8:
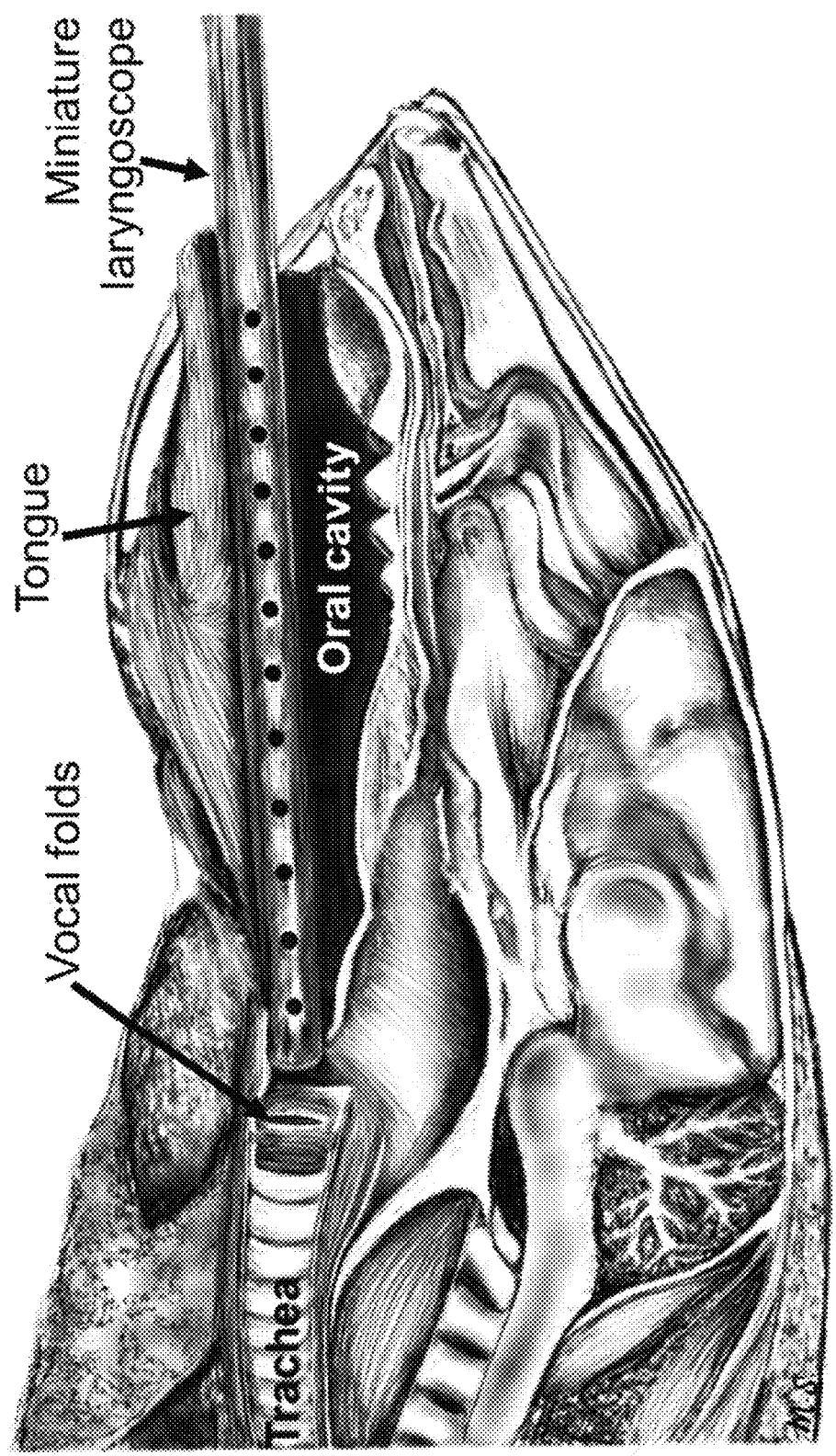
FIG. 8 is a schematic depiction of a transoral laryngoscopy in a mouse, wherein a sialendoscope with a modified protective sheath is inserted transorally to view the vocal folds of an anesthetized mouse positioned in dorsal recumbency, in accordance with various embodiments of the present disclosure.

Laryngoscopy was performed using a 0° sialendoscope (model# R11573A; Karl Storz) with a 1.1 mm OD fiberoptic shaft and 0.5 mm ID working channel. The working channel was connected to the air pulse system via PE tubing (1.58 mm ID). A customized miniature laryngoscope was attached to the endoscope base and secured to a manual control micromanipulator. The tongue was pulled outward with a gentle finger grip and the endoscope was inserted transorally (FIG. 8) and positioned so the VFs filled the entire field of view. Supramaximal air pulses were delivered to the arytenoid mucosa approximately once every 10 breaths for up to 20 minutes. The procedure was digitally recorded at 30 fps using a Storz Tele Pack X system. Upon procedure completion, mice were given one SQ injection of Banamine (2.2 mg/kg) for inflammation and pain prophylaxis and transferred to a 37° heating pad until complete emergence from anesthesia. Only mice with bilateral LAR responses were included in data analysis: healthy control mice (n=10), aging B6 mice (n=5), and ALS-affected mice (i.e., transgenic SOD1-G93A, n=4).

Example 3: Video Analysis of Bilateral LAR Responses

Figure 9:
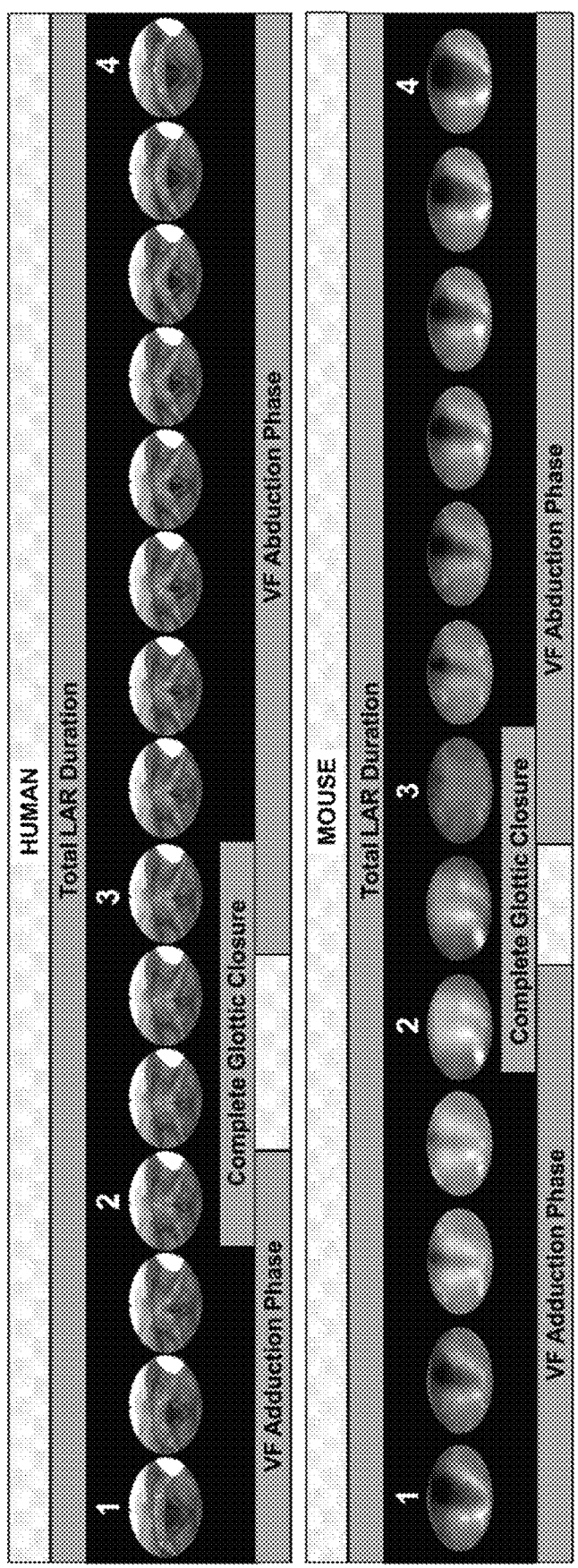
FIG. 9 is a depiction of certain aspects of the LAR metrics developed utilizing a method for determining physiological characteristics of the LAR response, in accordance with various embodiments of the present disclosure. Particularly, FIG. 9 exemplarily illustrates frame-by-frame sequences of the LAR that were recorded from a human and a mouse subject showing four distinct events which quantify particular LAR metrics in each species, and across species (VF=vocal fold), in accordance with various embodiments of the present disclosure.

Videos were analyzed on a computer using video editing software (Pinnacle Studio 14; Pinnacle Systems, Inc.). Using frame-by-frame analysis methods, we identified four novel LAR metrics: 1) VF adduction phase duration, 2) complete glottic closure duration, 3) VF abduction phase duration, and 4) total LAR duration. Our operational definitions are described in Table 1. Quantification of these metrics required identification of four distinct events within each bilateral LAR response: 1) rest frame preceding the first frame of VF adduction, 2) first frame of complete glottic closure (i.e., absent or smallest glottal gap), 3) final frame of complete glottic closure (i.e., frame preceding glottal gap reemergence at the onset of VF abduction), and 4) final frame of VF abduction (i.e., maximum glottal gap). Various combinations of paired comparisons of the 4 LAR events corresponded to the 4 novel LAR metrics of interest to this study. For example, the duration of time (ms) between events 1 and 2 corresponded to VF adduction phase duration, events 2 and 3 with complete glottal closure duration, 3 and 4 with VF abduction phase duration, and 1 and 4 with total LAR duration, as shown in FIG. 9.

All videos were initially viewed to identify and analyze up to 10 episodes of bilateral LAR responses for each subject. A second reviewer then independently re-analyzed each response in a blinded fashion, using only the LAR starting frames identified by the first reviewer. All value discrepancies were subjected to group consensus to resolve reviewer error.

Example 4: Statistical Analysis

Statistical analysis entailed independent t-tests for group comparisons of the means for each of the four LAR metrics. Two-sided tests were performed with IBM SPSS Statistics 21. A p-value <0.05 defined statistical significance.

Results

1. Young Healthy Humans and Mice

Figure 10:
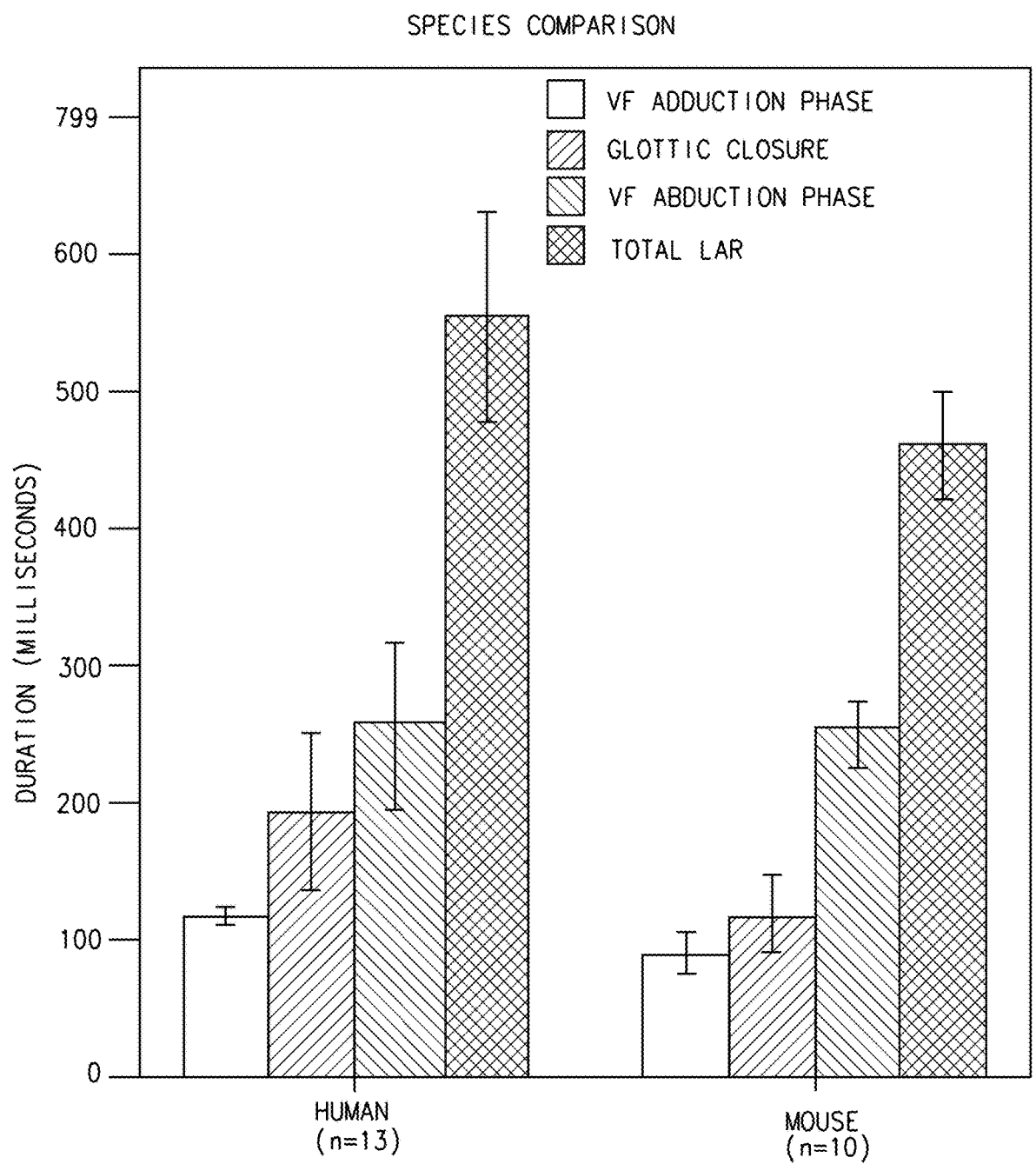
FIG. 10 exemplarily illustrates a combination of charts providing a graphic comparison, by species (human vs. mouse) of four specific LAR metrics: VF Adduction Phase; Glottic Closure Phase; VF Abduction Phase; and Total LAR duration. The pattern and timing of the four LAR metrics is similar between humans and mice (Error bars: plus/minus 1 standard error of the mean) (VF=vocal fold), in accordance with various embodiments of the present disclosure.

Multiple (3-10) bilateral LAR responses were elicited from each young human subject who tolerated nasolaryngoscopy (n=13; 6 males and 7 females) and from young control mice (n=10; 5 males and 5 females). The timing of the four metrics resulted in a stair-step pattern that is remarkably similar between both species (FIG. 10). There were no significant differences identified between mice and humans for each of the LAR metrics.

2. Mouse Models

Figure 11:
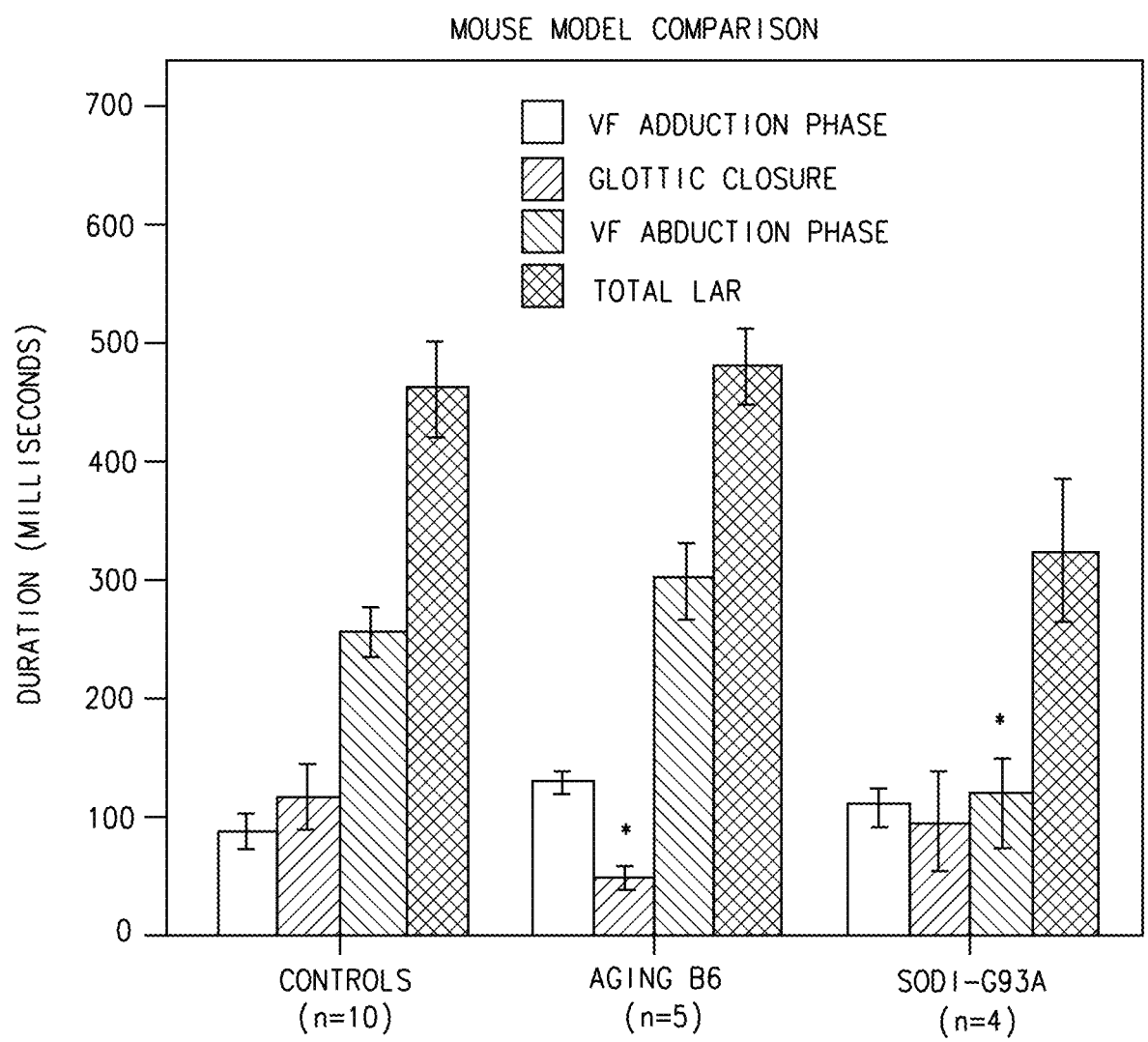
FIG. 11 exemplarily illustrates a series of charts providing a graphic comparison of LAR impairment. Compared to controls, aging mice and ALS-affected mice demonstrate significantly shorter durations of glottic closure and vocal fold (VF) abduction, respectively ($*P<0.05$) (Error bars: plus/minus 1 standard error of the mean), in accordance with various embodiments of the present disclosure.

FIG. 11 shows comparisons between the three groups of mice: healthy controls (n=10), aging B6 (n=5), and ALS-affected (n=4). Three to 10 bilateral responses were elicited from each mouse. Of the four LAR metrics, only glottic closure duration was significantly different between young and old B6 mice (T=2.37, p=0.037), which was shorter for old B6 mice compared to young controls. Mean VF adduction phase duration was noticeably longer for aging B6 mice compared to controls; however, statistical significance was not reached (T=−1.90, p=0.079). Comparisons between controls and ALS-affected mice revealed a significant difference for VF abduction phase duration (T=3.86, p=0.002), which was shorter for ALS-affected mice. Mean LAR duration was shorter for ALS-affected mice compared to controls; however, statistical significance was not achieved (T=1.97, p=0.072).

TABLE 1

Operational Definitions of Novel LAR Metrics.[a]

| LAR Metrics | Operational Definitions |
| --- | --- |
| VF adduction phase duration | The duration of time that it takes the VFs to adduct during a bilateral LAR response. The start frame is the "rest frame" that immediately precedes VF adduction after delivery of air pulse stimulation. The end frame is when the VFs approximate along the entire medial edge. In cases of incomplete VF medialization, the frame of maximal medialization (i.e., smallest glottal gap) serves as the end frame. |
| Complete glottic closure duration | The duration of time that the VFs remain approximated along the entire medial edge during a bilateral LAR response. The start frame is identical to the end frame described above for VF adduction phase duration (ie, when the VFs approximate along the entire medial edge; smallest glottal gap). The end frame is 1 frame preceding the emergence of a glottal gap between the medial edges of the VFs. |
| VF abduction phase duration | The duration of time that it takes the VFs to abduct during a bilateral LAR response. The start frame is identical to the end frame described above for glottic closure duration (i.e., one frame preceding VF abduction). The end frame is when the VFs reach maximum abduction prior to resuming the next rest breathing cycle. In cases of VF abduction phase hesitation for more than 3 consecutive frames, followed by additional abduction, the end frame is the first frame of VF abduction hesitation. |
| Total LAR duration | The duration of time between the VF adduction phase start frame and the VF abduction phase end frame. |

Abbreviations:
LAR, laryngeal adductor reflex;
VF, vocal fold.
[a]The number of frames between the start and end frames for each LAR metric is divided by 30 frames per second and converted to milliseconds It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the present disclosure without departing from their scope. While the dimensions and types of materials described herein are intended to define certain parameters of various embodiments of the present disclosure, the embodiments are by no means limiting and are exemplary embodiments. Many other embodiments will be apparent to those of skill in the art upon reviewing the above description. The scope of the various embodiments of the present disclosure should, therefore, be determined with reference to the appended claims, along with the full scope of equivalents to which such claims are entitled.

What is claimed is:

1. A system for delivering one or more pulses of pressure to the larynx of a subject to elicit a laryngeal adductor reflex (LAR) in the subject, the subject having a larynx comprising left and right vocal folds (VFs), said system comprising:

a pressure pulsing component configured to provide an adjustable pulse of pressure to the larynx;

a respiratory sensor component configured to measure the respiratory cycle of the subject that is utilized to control operation of the pressure pulsing component;

a control system component in functional communication with the pressure pulsing component and the respiratory sensor, the control system configured to:
generate a respiratory waveform based on the respiratory cycle measurements received from the respiratory sensor by the respiratory sensor;
analyze the respiratory waveform to determine a start of an inspiration of the subject;
apply a system operator defined delay to the start of inspiration; and
trigger the pressure pulsing component to deliver a pulse of pressure at the end of the delay from the start of inspiration to control the timing of pulses of pressure delivered by the pressure pulsing component in one or more respiratory cycles.

2. The system of claim 1 further comprising an endoscope, wherein the system is configured to utilize video data provided by the endoscope to detect closing and opening activities of the VFs during the respiratory cycle.

3. The system of claim 1 wherein one or more of the pressure pulsing, control system and respiratory sensor components is automated.

4. The system of claim 1 further comprising an air catheter unit in communication with the pressure pulsing component configured to assist in delivering pressure pulses to the larynx of the subject.

5. The system of claim 1 wherein the control system component is configured to adjust for temporal variation in the subject's LAR response.

6. The system of claim 3 wherein the control system component is configured to provide for automated delivery of pressure pulses in synchrony with one or more phases of the subject's respiratory cycle.

7. The system of claim 1 wherein the pressure pulsing component comprises an air pressure source in the form of an air cylinder, air cartridge, or mini air cartridge.

8. A method for performing a laryngeal adductor reflex (LAR) test on a subject, wherein the subject has a larynx comprising left and right vocal folds (VFs), said method comprising:
delivering at least one pulse of pressure to the larynx of a subject utilizing a pressure pulsing component of a pressure pulse LAR test system;
controlling at least one of a timing, a magnitude, and a number of pulses of pressure delivered by the pressure pulsing component in at least one respiratory cycle of the subject utilizing a control component of the pressure pulse LAR test system, the control component being in functional communication with the pressure pulsing component;
detecting at least one physiological characteristic of the subject's LAR response to the one or more pulses of pressure delivered to the subjects larynx utilizing video data provided by an endoscope of the pressure pulse LAR test system; and
utilizing the at least one physiological characteristic to determine at least one of an adduction phase duration, a glottic closure duration, a VF abduction duration, a total LAR duration, and a LAR onset latency.

9. The method of claim 8 wherein the method further comprises utilizing the at least one physiological characteristic to determine a pressure threshold to evoke a VF adduction.

10. The method of claim 8 wherein the method further comprises determining a VF adduction phase duration of the subject by establishing a time interval between a rest frame of the subject immediately preceding VF adduction through an end frame defined by one of the vocal folds approximating along the entire medial edge or in case of incomplete VF medialization, the moment wherein maximal medialization occurs.

11. The method of claim 8 wherein the method further comprises determining the subject's complete glottic closure duration by determining the time interval that the VFs remain approximated along the entire medial edge during a LAR response or, in case of incomplete VF medialization, the time interval of the smallest glottal gap.

12. The method of claim 8 wherein the method further comprises determining the subject's VF abduction duration by determining the time interval between one frame preceding the emergence of a glottal gap between the medial edges of the VFs and a frame wherein the VFs reach maximum abduction prior to resuming a next rest breathing cycle, or in cases of VF abduction phase hesitation, in which a predetermined number of consecutive frames defining a hesitation is followed by additional abduction, the time interval through a predetermined frame of the VF abduction hesitation.

13. The method of claim 8 wherein the method further comprises determining the subject's LAR onset latency by determining the time interval from pressure pulse delivery to the start of the LAR response.

14. The method of claim 8 wherein the method further comprises determining the subject's total LAR duration by determining the duration of time between the VF adduction phase start frame and VF abduction phase end frame.

15. The method of claim 8 wherein the method further comprises eliciting a laryngeal adductor reflex (LAR) response in the subject by providing the subject with one or more adjustable pulses of pressure from a pressure system component in functional communication with a control system component, utilizing the at least one physiological characteristic to detect the subject's LAR response, and determining the one or more physiological characteristics of the subject's LAR response to the pressure delivered.

16. The method of claim 8 wherein one or more of the pressure pulsing component, respiratory sensor component, and the control component is automated.

17. The method of claim 8 wherein the subject's larynx comprises an arytenoid mucosa, aryepiglottic fold, or other mucosal target at the entrance of the larynx, and the method comprises:
delivering a series of air pulses by an air pulse system to the arytenoid mucosa, aryepiglottic fold, or other mucosal target at the laryngeal entrance of the subject through a working channel of the endoscope having a tip,
adjusting the tip of the endoscope to ensure an adequate viewing field, and
determining one or more LAR metrics selected from the group consisting of VF adduction phase duration, glottic closure duration, VF abduction duration, total LAR duration, and LAR onset latency.

18. The method of claim 8 wherein the method further comprises utilizing the at least one physiological characteristic to determine the velocity or angles of motion of the subject's VFs during the LAR.

* * * * *